(12) United States Patent
Weiss et al.

(10) Patent No.: US 7,084,970 B2
(45) Date of Patent: Aug. 1, 2006

(54) INSPECTION OF TFT LCD PANELS USING ON-DEMAND AUTOMATED OPTICAL INSPECTION SUB-SYSTEM

(75) Inventors: Adam Weiss, Pickering (CA); Afsar Saranli, Toronto (CA)

(73) Assignee: Photon Dynamics, Inc., San Jose, CA (US)

(*) Notice: Subject to any disclaimer, the term of this patent is extended or adjusted under 35 U.S.C. 154(b) by 286 days.

(21) Appl. No.: 10/846,457

(22) Filed: May 14, 2004

(65) Prior Publication Data

US 2005/0254045 A1    Nov. 17, 2005

(51) Int. Cl.
*G01N 21/00* (2006.01)

(52) U.S. Cl. .............................. 356/237.5; 356/237.4; 356/239.2

(58) Field of Classification Search ...................... None
See application file for complete search history.

(56) References Cited

U.S. PATENT DOCUMENTS

| | | | |
|---|---|---|---|
| 4,247,203 A | 1/1981 | Levy et al. | |
| 4,247,208 A | 1/1981 | Fulkerson et al. | |
| 4,347,001 A | 8/1982 | Levy et al. | |
| 4,589,140 A * | 5/1986 | Bishop et al. | 382/148 |
| 4,805,123 A | 2/1989 | Specht et al. | |
| 4,843,312 A | 6/1989 | Hartman et al. | |
| 4,926,489 A | 5/1990 | Danielson et al. | |
| 4,983,911 A | 1/1991 | Henley | |
| 5,097,201 A | 3/1992 | Henley | |
| 5,124,635 A | 6/1992 | Henley | |
| 5,179,345 A | 1/1993 | Jenkins et al. | |
| 5,333,052 A | 7/1994 | Finarov | |
| 5,414,374 A | 5/1995 | Brunner et al. | |
| 5,546,013 A | 8/1996 | Ichioka et al. | |
| 5,570,011 A | 10/1996 | Henley | |
| 5,612,626 A | 3/1997 | Golladay | |
| 5,615,039 A | 3/1997 | Henley | |
| 5,650,844 A * | 7/1997 | Aoki et al. | 356/237.2 |
| 5,801,824 A * | 9/1998 | Henley | 356/237.2 |
| 5,864,394 A | 1/1999 | Jordan et al. | |
| 5,923,430 A * | 7/1999 | Worster et al. | 356/394 |
| 6,282,309 B1 | 8/2001 | Emery | |
| 6,437,596 B1 | 8/2002 | Jenkins et al. | |

OTHER PUBLICATIONS

Golladay et al. "Electron-beam technology for open/short testing of multi-chip substrates," IBM Journal of Research and Development 34:250-259 (1990).

Jenkins et al. "Functional Testing of TFT/LCD arrays," IBM Journal of Research and Development 36:59-68 (1992).

* cited by examiner

*Primary Examiner*—Michael P. Stafira
(74) *Attorney, Agent, or Firm*—Townsend and Townsend and Crew LLP

(57) ABSTRACT

In an inspection system for electrical and electro-optical inspection of TFT-LCD panels, a fine resolution area imaging camera with a pulse illumination source disposed to scan the region and operative capture images of the region illuminated with pulses of short illumination and automatically maintained in focus while continuously scanning in order to resolve points of defects.

11 Claims, 6 Drawing Sheets

INSPECTION OF TFT LCD PANELS USING ON-DEMAND AUTOMATED OPTICAL INSPECTION SUB-SYSTEM

CROSS-REFERENCES TO RELATED APPLICATIONS

Not Applicable

STATEMENT AS TO RIGHTS TO INVENTIONS MADE UNDER FEDERALLY SPONSORED RESEARCH OR DEVELOPMENT

Not Applicable

BACKGROUND OF THE INVENTION

This invention relates to the inspection of flat electronic circuit patterned media at various stages of production using electrical, electro-optical and optical techniques. More specifically, this invention relates to the automated electrical, electro-optical and optical inspection of flat electronic substrates, such as thin film transistor (TFT) arrays (the main component of the liquid crystal flat panel displays (LCD)). In particular, the focus is on the inspection of high density thin film transistor (TFT) liquid crystal display (LCD) panels, deposited on large sheets of glass.

During the manufacturing of TFT LCD panels, large clear sheets of thin glass are used as a substrate for the deposition of various layers of materials to form electronic circuits that are intended to function as a plurality of separable, identical display panels. This deposition is usually done in stages where, in each stage, a particular material (such as metal, Indium Tin Oxide (ITO), Silicon, Amorphous Silicon etc.) is deposited over a previous layer (or upon the bare glass substrate) in adherence to a predetermined pattern. Each stage includes various steps such as deposition, masking, etching and stripping.

During each of these stages and at various steps within a stage, many production defects may occur that have electronic and/or visual implications on the final LCD product performance. Such defects include for example circuit shorts, opens, foreign particles, misdeposition, feature size problems, over- and under-etching. The most common defects, shown in FIG. 1, include metal protrusion 110 into ITO 112, ITO protrusion 114 into metal 116, a so-called mouse bite 118, an open circuit 120, a short 122 in a transistor 124, and a foreign particle 126.

In the primary intended application domain of TFT LCD panel inspection, the article defects that are the subject of detection are small (down to individual micrometers) requiring demanding defect detection limits.

Mere detection of defects is insufficient. Detected defects must also be classified as process defects, i.e., minor imperfections which do not undermine the performance of the finished product but which are an early indication of the array manufacturing process drifting out of optimum conditions, reparable defects which can be repaired to improve the array production yield, and finally killer defects which disqualify the TFT array from further use.

A broad range of techniques have been used to detect and classify the aforementioned defects. The techniques belong to the three broad categories, namely electrical, electro-optical and purely optical.

Electrical and electro-optical techniques require the subject of inspection to have some measurable electrical or electromagnetic properties. This is the case for the primary intended application domain of inspecting TFT LCD panels. The subject can be excited by electrical means, and the resulting electrical or electromagnetic behavior be measured and recorded. The behavior is then compared with the known normal behavior to determine the presence or absence of abnormalities in the subject being inspected.

For these techniques, the physical size or visibility of the defect causing the electrical and/or electromagnetic anomaly is often not a limiting factor for detection. The defect will be detected as long as it has a significant, measurable impact on the electrical and/or electromagnetic behavior of the circuit on the subject being inspected. The inherent limitation of this type of inspection however is that only defects that affect the electrical and/or electromagnetic behavior of the circuit can be detected. Other anomalies, independent of size, are missed by the inspection system. In addition, some of these defects may affect an area which is much larger than the physical defect size. Hence, in some common cases, an electrical or electro-optical inspection technique would detect a defect signature which does not necessarily correspond to the physical defect that is the source of the anomaly on the subject being inspected.

Purely optical inspection techniques, referred to as automated optical inspection (AOI), can both detect and locate defects independent of their electrical properties, provided they are visible under the chosen optical setup. However, there is often a significant limit on the size of the defects that can be detected in a reasonable amount of time. Better detection limits (smaller defects) and shorter inspection times are both very important goals. However for AOI systems, these are always conflicting goals and must be compromised. What is achievable is limited by the available technology of imaging and processing hardware. The inspection time also scales up with the size of the article being inspected. Therefore, for AOI applications, the resulting high sensitivity systems are often slow and faster systems have coarser imaging resolutions and hence lower detection sensitivities.

Electrical and electro-optical inspection methods are particularly attractive because of their ability to detect electrical defects even when they are very small or when they are buried under other layers of deposition and hence are optically invisible. This is especially true for the final inspection of the TFT LCD panels after all layers of material have been deposited, the LCD panel is fully functional and can be electrically excited. Therefore, providing an improvement for overcoming the defect localization and classification limitations of the electrical and electro-optical inspection methods is an important problem.

There is a variety of methods and apparatus in the prior art for detecting abnormalities in flat patterned media and in particular in glass plates deposited with TFT LCD flat panels. A first category of such methods is the electrical testing of the circuitry which is formed by the material deposition on the flat media. These technique can be used when the pattern in question forms a complete or partial electrical circuit that can be excited and whose electrical variables can be measured.

In an article "Functional Testing of TFT/LCD Arrays", IBM Journal of Research & Development, Vol. 36, No. 1, January 1992; Jenkins et al. argue that the defects in charge holding capabilities of individual TFT LCD pixels, as well as the presence of a number of other defects, can be detected by selectively charging the pixels and discharging them through a sensing circuit. In this way, the measurement is of how much of the originally stored charge can be recovered.

A sensing aspect of the method and its connections to the LCD panel pixels are described in detail in U.S. Pat. No. 5,179,345 to Jenkins et al. A TFT LCD panel defect detection apparatus is described in U.S. Pat. No. 5,546,013 to Ichioka et al.

The aforementioned testing method requires galvanic connections to all gate and data lines of a TFT LCD panel structure to be able to address and electrically test individual pixels. This limitation makes for contact hardware that is expensive and difficult to maintain. An improvement over the method to reduce the number of required contacts is proposed in U.S., Pat. No. 6,437,596 B1 to Jenkins et al.

Another type of electrical testing of such circuits on flat media is by means of electron beams irradiated to the surface being inspected. A number of solutions using electron beams make use of the basic principles of Scanning Electron Microscopy (SEM). In this method, by means of irradiating the circuit features with a low energy electron beam and recording the energy level of the secondary electrons scattered from the said circuit features, a voltage distribution on the surface being inspected can be generated. This generated voltage map can be used to detect the presence and type of electrical defects on the surface.

U.S. Pat. No. 4,843,312 to Hartman et. al., describes the general approach of using an energy beam (or particle beam) to test for the defects in an TFT LCD circuit structure.

U.S. Pat. No. 5,414,374 to Brunner et al. also describes a particle beam tester for LCD panels. In this case, the plane electrodes of the LCD pixels are targeted by the beam to create a potential on the electrode. In a following measurement cycle, this potential is measured by means of the scattered secondary electrons of either the same or a second beam and compared to the nominal values. The switching element is also activated during the measurement period to provide a time varying potential, which can also be measured and compared to the nominal behavior.

Another rather different application of the electron beam testing is through charging or discharging the circuit features by means of the electron beam sequentially directed to localized sections of the said circuit features. For example, the individual pixels in a TFT LCD panel pixel array are excited with a low energy electron beam and the induced currents measured to determine the presence of electrical defects in the structure. In an article named "Electron-Beam Technology for Open/Short Testing of Multi-Chip Substrates," IBM Journal of Research & Development, Vol. 34, No. 2/3, March/May 1990, Golladay et al. describe this technique. A more recent U.S. Pat. No. 5,612,626 to Golladay et al., describes an electronic substrate defect detection system based on electron beam technology.

The second category of defect detection methods is that of electro-optical techniques. In this category of methods, the electrical and/or electromagnetic behavior of the circuit is converted into an optically observable (typically through visible light or e-beam reflection formed through a suitable modulator. The output of the modulator is then imaged through optical means to form images representative of the electrical behavior of the inspected circuits. In particular, the images of the electric field and hence the voltage distribution of the inspected circuits can be generated in the form of voltage maps These images can then be used to detect and identify the electrical defects on the surface.

U.S. Pat. Nos. 4,983,911, 5,097,201 and 5,124,635 to Henley describe the principles of an electro-optical light modulator and associated imaging means where the voltage and the resulting electric field from a surface under test are used to modulate the optical properties of a suitable liquid crystal variant structure. An optical image is thus created and recorded by means of an image capture device. An improved version of this electro-optical modulator with its manufacturing method is disclosed in a later U.S. Pat. No. 5,615,039 to Henley.

U.S., Pat. No. 5,570,011 to Henley describes a complete method of using this electro-optical sensing element in a testing arrangement for testing electronic devices, which can be excited to be in known electrical states. This method has been successfully used in the electro-optical testing of the electrical functionality of the TFT LCD panels at the final stages of their production before being assembled and filled with liquid crystal.

The other major category of defect detection methods, Automated Optical Inspection (AOI) is based on optical imaging at the required magnification and resolution and using hardware/software image processing techniques to detect defects out of the expected usual variations of the article being inspected. The anomalies detected are not limited to electrically significant defects but rather they are limited to optically discernible objects determined by the given optical configuration, the imaging magnification and the resolution of the system. The resolution also determines the complexity and the operational speed of such a system.

The basic principle of performing such an automatic inspection is based on imaging the article being inspected with a chosen magnification and resolution and then digitizing the image information using an image capture device such as a CCD or CMOS sensor. The captured images may be used to build references of the normal variations of the surface of the article being inspected and perform defect detection based on comparisons with a reference. The comparison procedure may be done in the spatial domain where spatial pattern comparison techniques such as image subtraction are used to detect the deviation of a test image from a reference. Alternatively, the comparison can be done in the feature domain with suitably chosen representative features. In this latter case, both the test article and reference are represented by sets of features derived from the images. The comparison is also performed in this chosen feature space.

There exist many approaches for optical inspection. For example, In U.S. Pat. Nos. 4,247,203 and 4,347,001 to Levy et al. describe an automatic optical photomask inspection apparatus using a spatial pattern comparison technique to detect defects in photomasks of repeating circuit dies.

U.S. Pat. No. 4,805,123, to Specht et al., discloses an improved method of inspecting surfaces with such repetitive patterns by means of spatial pattern comparison at sub-pixel resolution. A detection sensitivity close to the imaging resolution is achievable through careful sub-pixel alignment of the reference and test images. Such detection sensitivity is normally not possible because of the aliasing noise (also called pixelation noise) in the image sampled at a particular resolution. The method has been used in silicon wafer inspection as well as TFT LCD inspection.

There have also been other solutions proposed for photomask and integrated circuit die pattern inspection. These have been described for example in U.S. Pat. No. 4,926,489 to Danielson et al., U.S. Pat. No. 5,864,394 to Jordan et al., and U.S. Pat. No. 6,282,309 to Emery.

Application of the automated optical inspection technology to the inspection of TFT LCD panels has consisted of the scaling up of the techniques well established for the inspection of integrated circuit dies. However, other techniques addressing specific problems of the application domain, such as improving material contrast have also been disclosed. For example, U.S. Pat. No. 5,333,052 to Finarov describes a phase contrast imaging technique which is especially useful for improving the contrast, and hence the detectability of transparent materials (such as ITO) in TFT LCD panels.

AOI systems may be capable of detecting and imaging defects of electrical nature and of non-electrical nature and hence can be used for process control purposes by detecting defects which do not immediately lead to functional failures. However, their performance and inspection time is a function of the instrument operating resolution.

Because many defects causing severe electrical failures in circuitry are very small as compared to the entire surface of the article being inspected, the requirement to detect these severe defects leads to instruments with high optical operating resolution. This, in turn, results either in a very expensive instrument, a very slow instrument or both. Even with the most expensive hardware, there is a limit on the achievable inspection speed determined by the available hardware technology. These limitations are especially significant for the preferred application area of TFT LCD panel inspection where the sizes of flat material plates deposited by TFT LCD panels are getting much larger than the circuit feature sizes involved.

Therefore, there is demand for the aforementioned electrical and electro-optical inspection technologies which can detect electrically significant defects independent of their physical sizes. However, the electrical and electro-optical systems face difficulty: For certain types of defects, the electrical signature of the defect may cover a much larger zone than the physical cause of the defect. For example, a short from a data line to the common line in an TFT LCD panel circuit will ground the entire data line and hence will result in a defect signature which covers the entire zone occupied by the data line. This inspection does not give localization information for the defect, and it is a major drawback in such systems. Defect localization information is useful in order to monitor re-occurrences of defects for process control purposes in order for an operator to manually review the nature of the defect through an optical microscope, or for an automated classification sub-system to image and process the defect. If a repair instrument is involved in the process, the localization information is further used to find and repair the defect.

An earlier U.S. patent application Ser. No. 10/223,288 to Clark et al., entitled "Integrated Visual Imaging and Electronic Sensing Inspection Systems" discloses the generic concept of augmenting a non-AOI inspection instrument with an integrated visual imaging (AOI) channel to concurrently perform the scan of the entire surface of the subject being inspected by both independent channels with the aim of combining the detection and classification results.

The typical prior art process flow for defect detection and repair is outlined in FIG. 2. The process is valid not only for Non-AOI inspection systems but also for AOI systems. In operation the article being inspected arrives from the previous process step ( Step 210) and is directed to the defect detection system 212 to be scanned for production anomalies in the article. After the defect detection system operates on the article, an output is generated that is a list of defects which are identified on the article being inspected.

Depending on the capabilities of the defect detection system, the defects may be precisely localized defect points or loosely localized defect zones which may cover a large area. For example, certain electrical testing methods are not able to determine the precise location of a line short, since the resulting electrical anomaly affects the entire line and not only the area where the physical defect occurred.

In the event no defect could be identified (Step 214) by the defect detection step (in system 212), the article is passed to the next process step (Step 224). If one or more defects are identified, then a decision is made about whether each of these defects is repairable (Step 216) by an appropriate repair system 218. Depending on the capabilities of the inspection and repair systems 212, 218, this decision can be made either in the inspection system 212 or in the repair system 218. For example, some inspection systems have the capability to perform automatic review and classification based on user specifications to classify the defects based on whether they are repairable or not.

Repairable defects are processed by the repair system and if successful (Step 228), the inspected panels are either passed to the next process step (Step 224) or are subjected to an alternative processing (Step 220) and are diverted to an alternative process flow (Step 226). The exact handling of non-repairable defective samples is usually manufacturing plant dependent. Depending on the plant strategy, alternative processing and subsequent process flow may simply lead to scrapping of the entire substrate plate, scrapping only the defective panel on the substrate or stripping and recycling the entire substrate plate to the beginning of the process. While the articles being inspected are propagated through the process, the information about the identified defects is stored and communicated through a database 228 accessible to both the inspection and repair systems.

What is needed is a panel inspection system that specifically addresses the limitation of most of the non-AOI systems such as those based on electrical and electro-optical techniques, to accurately locate certain type of defects before these defects are reviewed by the user or by an automated classifier.

Only one such technology has been introduced in the industry. In Korea, Charm, Inc. has recently developed a station to automatically locate defects in a panel in order to facilitate repair. The apparatus is an improvement in a process operating in a repair instrument. The apparatus uses a separate TDI line-scan camera as separate associated optics operating independently of the main review and repair optics of the repair station. The apparatus employs a coarse object plane pixel resolution such that sub-pixel interpolation is required to secure a desired fineness of resolution and detection sensitivity. The imaging is one-dimensional in nature, with two notable results. The image cannot be captured instantaneously and a two different scans at orthogonal angles must be performed to detect defects along two directions. Therefore, the line scan camera itself must be physically rotated between the two scanning directions.

SUMMARY OF THE INVENTION

According to the invention, in an inspection system for electrical and electro-optical inspection of TFT-LCD panels, automated inspection is enhanced by providing, as part of the regular review channel an on-demand fine resolution image AOI scan of a limited section of the subject being inspected by capturing during a scanning process an accurate fine resolution two-dimensional image of a specific region using a series of short pulse of illumination that is captured by a spatial imaging device in order to help the defect localization and classification aspects of electrical or electro-optical inspection system. More than one point defect can be identified by the process as the process captures multiple images. An apparatus according to the invention can be employed as a standalone instrument or incorporated into inspection stations or repair stations to accurately locate certain type of defects before these defects are reviewed by the user or by an automated classifier. Due to the fine imaging resolution, there is no need for subpixel interpolation.

In a specific embodiment, a high speed area scan camera capable of capturing more than 60 frames per second is operative to scan at a speed greater than 30 mm/second while capturing flash lamp images having an exposure duration of less than about 20 microseconds and preferably less than eight microseconds. A hardware auto-focus sensor using triangulation and sharing the same optical path as the imaging scan camera provides fast continuous in-focus tracking for the imaging function.

The on-demand functionality operates sequentially with the non-AOI detection function and/or repair function and is performed on a pre-determined limited zone to locate and image defects therein. Specific embodiments of this invention may be in the form of the functional augmentation of non-AOI inspection instruments as well as the functional augmentation of repair instruments which operate in association with the said non-AOI inspection instruments.

The invention will be better understood by reference to the following detailed description in connection with the accompanying drawings.

DETAILED DESCRIPTION OF THE INVENTION

In an inspection system or in a group of systems consisting of inspection and repair equipment, a well defined process is used to determine how exactly the inspection and the subsequent optional repair operations will be performed. This process describes the roles of the sub-systems involved in the inspection and repair operations and the sequence of actions which will be performed on the article being inspected.

The present invention proposes to augment the instruments to add an improvement employing an AOI-on-demand sub-system.

The improved flow and added abilities to quickly identify defects with the added sub-system are considered to be a primary contribution of the present invention.

Figure 1:
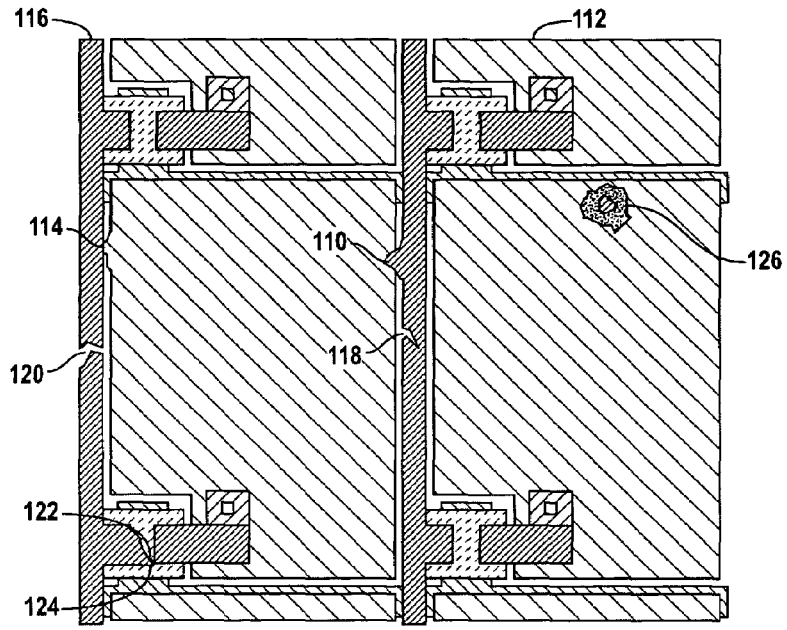
FIG. 1 is a diagram of an article under test illustrating types of defects.
Figure 2:
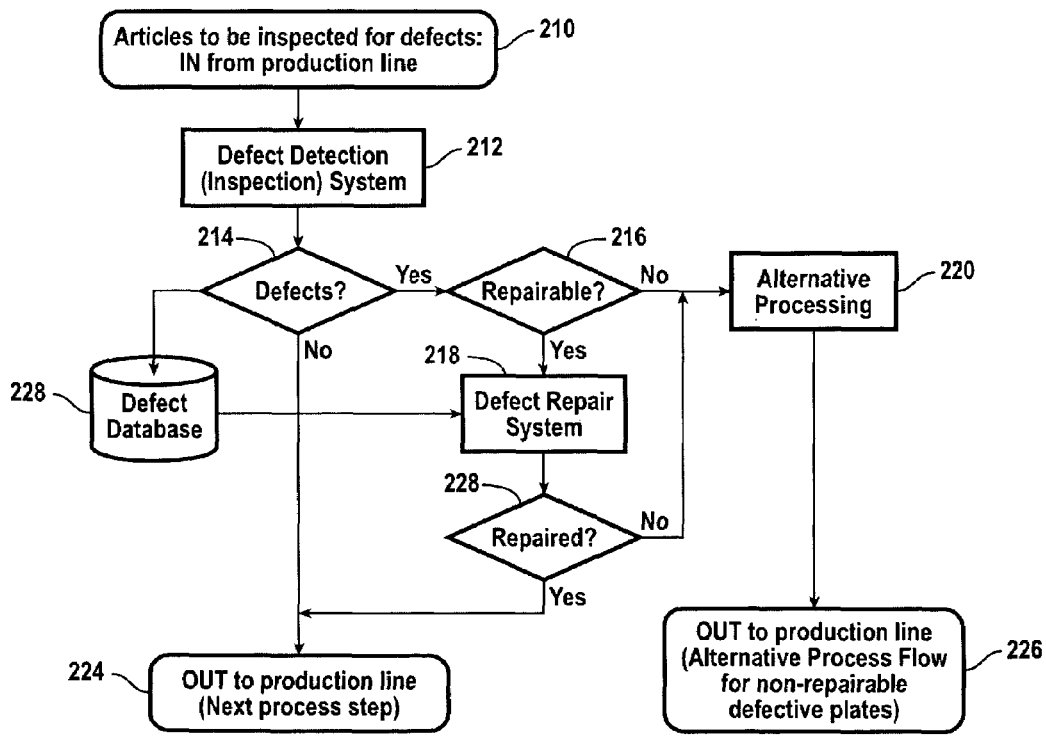
FIG. 2 is a flow diagram around a defect inspection system and a defect repair system.
Figure 3:
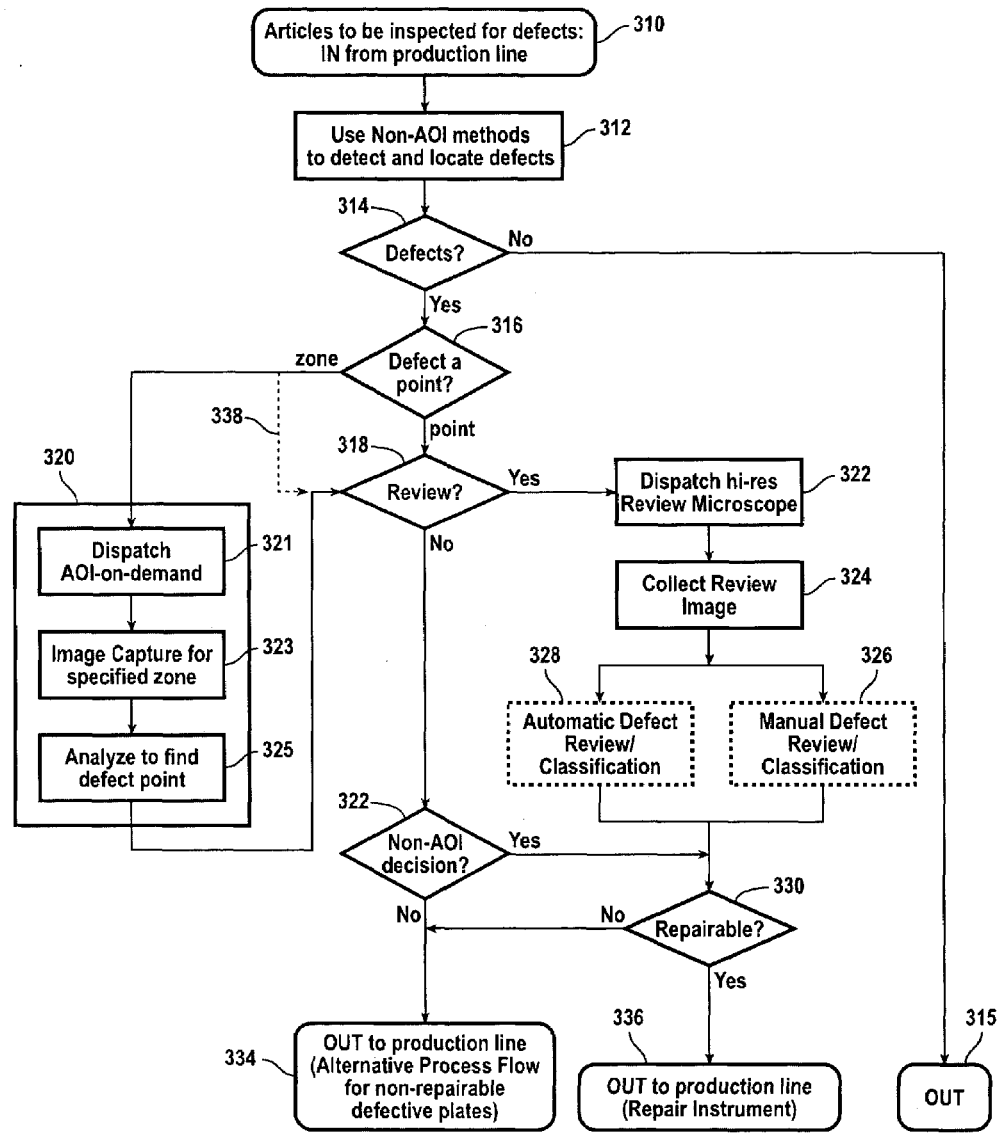
FIG. 3 a detailed view of this process on the defect detection instrument side.

In FIG. 3, a specific embodiment of the AOI-on-demand process is presented where the new functionality is integrated into the inspection side of the process and into an inspection instrument. Articles subject to defect inspection are input (Step 310) to an inspection instrument (represented by processes beginning at Step 312). The inspection instrument scans the article surface for defects (Step 312). If no defects can be located ( Step 314), the article is passed to the following process step (Step 315), skipping the repair instrument or instruments. If defects are located (Step 314), they are subjected to the review step (beginning at Step 316) if the instrument is equipped with defect review hardware.

The non-AOI inspection equipment often indicates defects with electrical signatures spanning a single spatial point, i.e., a zone. The known art treats both types of defects in the same way, i.e., they are either reviewed with an optical microscope for classification or are treated according to the non-AOI decision criteria (such as the type of electrical defect identified by the system) to decide whether they are repairable or not. These steps are incorporated into the present invention as Step 316 and path 338, Step 318, Step 332 and Step 330.

The defect review on the inspection instrument is done by dispatching a fine resolution optical microscope to the defect location (Step 322) and collecting a review image for the selected field of view (Step 324). The image is then either viewed by a human operator (Step 326) or can be subject to an automatic classification system (Step 328) to make a decision on the type and severity of the defect. The defect is again assessed as being repairable (Yes) or killer (No) (Step 330) and the panel is dispatched either to the repair instrument (Step 336) or diverted toward an alternative process flow (Step 334).

The known art provides that if only a zone can be identified for the defect, then a difficult manual review process is initiated. For example a line short may mean that the operator needs to scan a line spanning the entire panel length or width to observe the physical defect through the microscope and make a decision on defect severity, which is, in most cases, an impossible task for a high magnification microscope, since a prohibitive amount of time is required to cover the zone and locate the defect. In the best case, the operator may switch between microscope magnifications and try to locate the defect in a smaller magnification. This also involves substantial operator time.

Automatic classifiers on the other hand usually are designed to work on a frame of an image and cannot cope with such cases where the exact location of the defect is not known.

According to the invention, when the electrical signature of a defect is a "zone" or a region, rather than a localized point, an AOI-on-demand process 320 sub-system is activated. An optical imaging system of suitable magnification and resolution is dispatched to scan the zone indicated by the non-AOI inspection to cover this entire zone (Step 321), and the collected image stream is captured and stored in system memory (Step 323) for further use or analysis. The image stream is processed by dedicated image processing hardware/software to detect and accurately locate the physical defect(s) responsible for the original electrical defect detected by non-AOI methods (Step 325). Once the defect is resolved into a spatially localized point, it is handed over to the review processing (Step 318).

Figure 4:
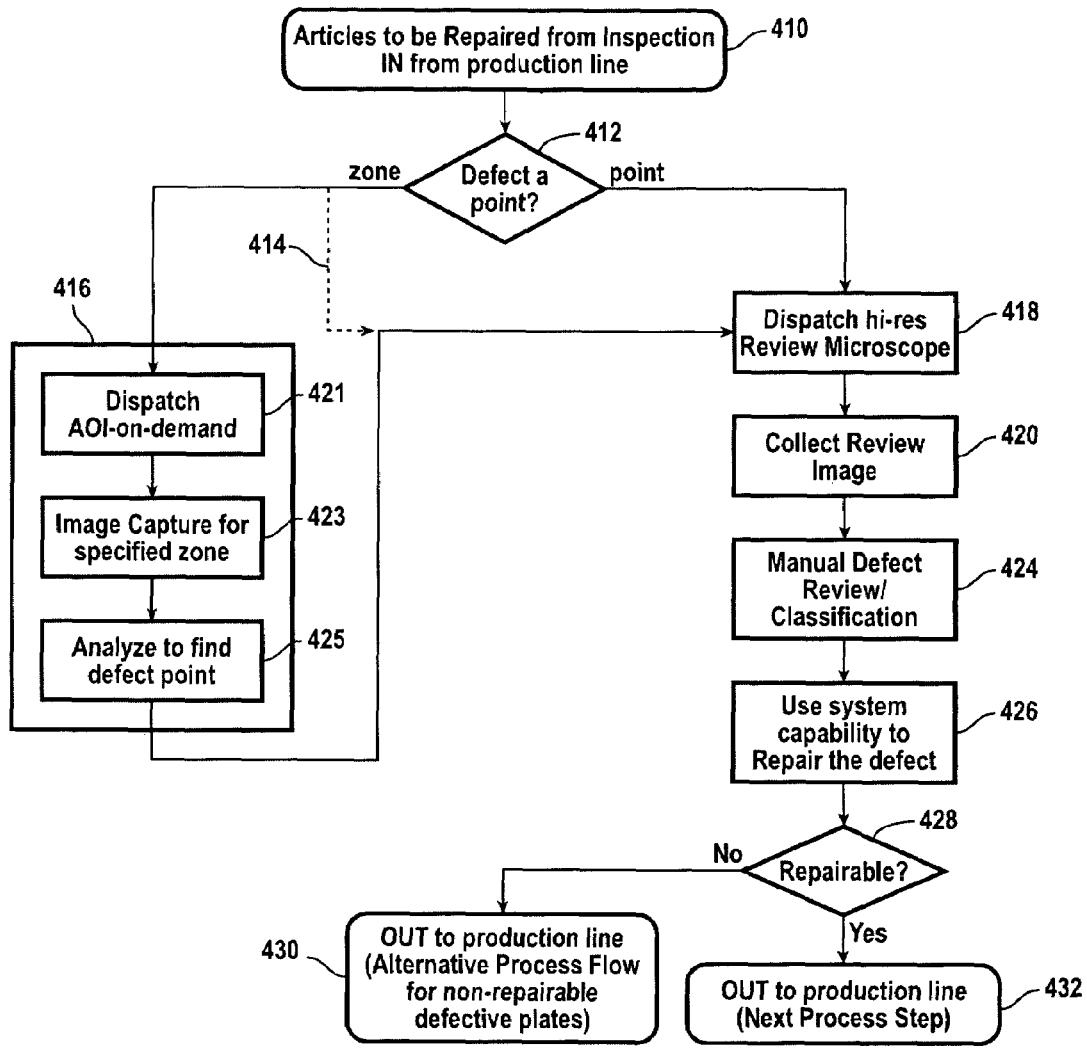
FIG. 4 presents a detailed view on the defect repair instrument side.

In FIG. 4, another embodiment of the invention is illustrated where the new AOI-on-demand functionality is integrated into the repair side of the process, namely on a repair instrument. The article subject to repair comes to the repair system from an earlier process step (possibly directly from inspection step 336, FIG. 3) (Step 410). The defect information is typically communicated to the system through a common database which was earlier updated by the inspection system (Steps 326 or 328, FIG. 3).

(In the known art, a repair instrument operates such that a defect, independent of whether it covers a point or a zone, is sent for review (Step 412, path 414 to Step 418). This review on the repair side of the process has in general been manual. An operator selects the defect to be repaired. A high magnification, high resolution optical microscope is dispatched to the defect location (Step 418), and the operator is presented with the image of the defect (Step 420). The operator decides how to repair the defect and takes the necessary action to do so (Steps 424, 426), forwarding the repaired item to the next process step (Step 432). If the defect could not be repaired (Step 428), the item is diverted to an alternative process flow (Step 430) to deal with the non-repairable defective panel.)

(When the defect can only be identified as a zone, the operator according to the known art has the task of manually scanning the entire zone for the actual physical defect and then attempting to repair it. This demands substantial operator time and has a direct negative impact on the repair throughput.)

The present invention, in a further embodiment, improves process by adding a specific AOI-on-demand capability. This is done by replacing the direct link (Path 414) by a process (Step 416). When the defect involved has a signature covering a zone rather than a localized point, the AOI-on-demand functionality is activated. An optical imaging system of suitable magnification and resolution is dispatched to scan the zone indicated by defect information to cover this entire zone and store the collected image stream in system memory (Steps 421, 423). The image stream is processed by image processing hardware/software to detect and accurately locate the physical defect(s) responsible for the original electrical defect zone (Step 425). Once each defect is resolved into a spatially localized point, it is handed over to the rest of the review and repair processing (beginning at Step 418).

The primary contribution of the invention is to improve the process through which the inspection and/or repair instruments operate in order to improve the throughput of the process involving-these instruments. Preferred hardware embodiments for the AOI-on-demand are examples to how the functionality can be incorporated into the instruments.

In a specific hardware embodiment of the present invention, a dedicated imaging channel of suitable magnification is used in conjunction with an area scan image capture device of matching resolution and a strobed flash lamp assembly as the AOI-on-demand sub-system. The particulars of this imaging channel optical arrangement are illustrated schematically in FIG. 5. All components of an area scan camera 500 are arranged along a central optical axis 510 and an illumination axis 528. A microscope objective 526 and a tube lens 518 are placed for viewing in the optical setup, and an area scan image capture device (e.g., a CCD or CMOS device) 514 is placed at the image plane of the compound (objective 526 and tube lens 518) image system. A sensor 514 is enclosed in a camera arrangement 512. During the image capture process, the article being imaged (not shown) is illuminated with a fast strobed flash-lamp 522 through illumination optics 520. The duration of illumination is typically on the order of less than 20 microseconds and preferably less than 8 microseconds for a scanning speed of 30 mm per second. The illumination is coupled with the main optical axis by means of a beam splitter 524, and the whole structure is mounted on an inspection or repair instrument (not shown) through a mounting plate 516. The optical apparatus according to the invention is mounted on the mounting plate 516 so that it can be translated relative to the target during operation, i.e., the target can be translated while the optics remain fixed or visa versa.

An area scan camera 500 combined with strobed illumination offers a number of advantages. The area scan camera 500 enables one to perform image collection along any scanning direction, since the area scan sensor 514 is not a direction sensitive image capture device as is the case for line-scan imaging devices. However, in general, the area scan imaging sensor is sensitive to the presence of motion and ideally should be used only while the camera is stationary. This drawback is alleviated by the use of a short pulse strobed flash-light illumination. The short pulse of high intensity light generated by this illumination scheme freezes the motion and enables the capture of a series of sharp images while the imaging channel assembly is in motion. This process implies an inherent robustness of image sharpness against the presence of vibration within the instrument. The short duty cycle of the flash-lamp also minimizes illuminator power consumption and extends the expected life of the bulb. Such a flash-lamp is smaller in size and lighter as compared to any alternative continuous illuminator.

Figure 5:
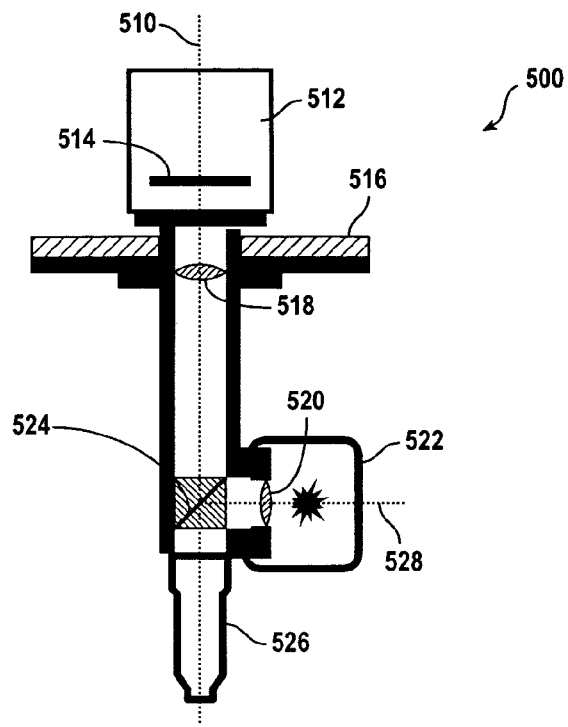
FIG. 5 is a side cross-sectional view of an optical imaging device according to one embodiment of the invention.

The optical arrangement illustrated in FIG. 5 is only one particular hardware embodiment of the present invention. Other embodiments are also possible and are discussed below.

Figure 6:
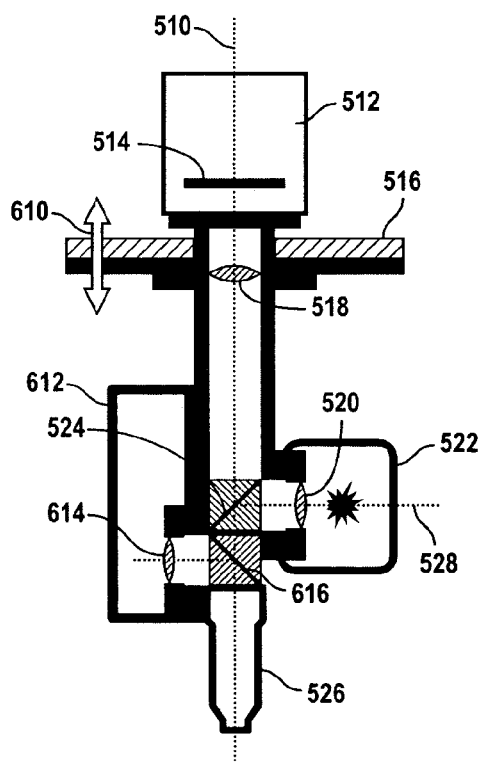
FIG. 6 is a side cross-sectional view of an optical imaging device according to another embodiment of the invention in which hardware auto-focus is employed.

FIG. 6 illustrates an embodiment of the invention where hardware-based tracking auto-focus is integrated into the imaging channel. In this embodiment, an auto-focus mechanism 612 uses for example triangulation to determine position and the imaging channel is mechanically capable of maintaining best focus through controlled motion 610 along the z-axis relative to the platform 516 supporting the entire assembly. The translation can be effected by such alternatives as a stepper motor or a voice-coil driving the entire stage or by voice coil actuation of the microscope objective 526. The hardware in-focus sensor 612 is mounted to the column and used to detect z-axis position and focus state. The in-focus sensor 612 is integrated into the imaging channel through a beam-splitter 616 and associated optics such as lens 614 directing the image to focus detection and control components (not shown) of the type used in a conventional camera. Controller elements can be mounted on the imaging channel or deployed in a separate housing, the output of which drives a servo to control mechanical positioning of the whole mechanism or at least of a lens element.

Figure 7A:
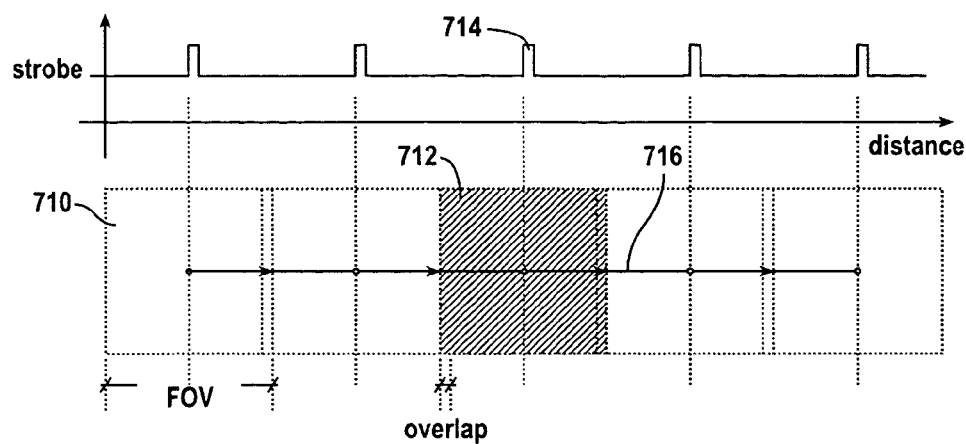
FIG. 7(a)–7(c) is an illustration of the strobed area scan imaging process according to the invention.
Figure 7B:
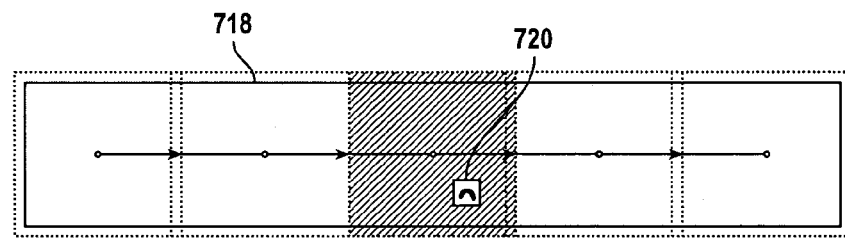
Figure 7C:
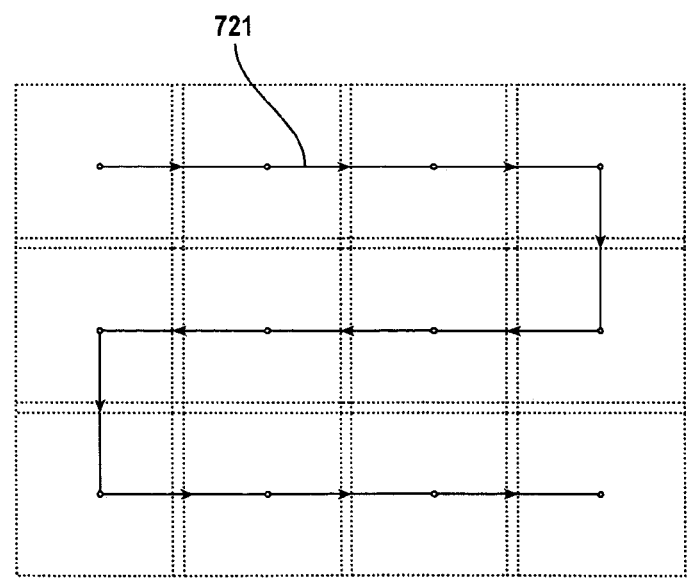

FIGS. 7(a), 7(b) and 7(c) illustrate the operation of the area scan imaging channel with strobed flash light illumination according to the invention. The imaging channel covers a specific field-of-view-FOV 710 with fine resolution, as represented by the area encompassing the center point of the image at the moment of the trigger signal 714 for the strobe pulse. As the imaging channel is moved along a specified motion path 716 or 722, strobed flash light illumination triggered by the periodic positional trigger signal 714 freezes an image along the motion of the channel and captures a sharp image of the area being scanned. Each FOV captured by the flash light illumination overlaps by a small area 712, typically on the order of 1%.

FIG. 7(b) illustrates the process of resolving a specified defect zone into a defect point. A zone or region 718 extending over several fields of view (FOV) along a motion trajectory is scanned with and the imaging channel instrument (FIG. 5 or 6) captures a sequence of fine resolution images to cover the entire region. Each captured image is processed by image processing and defect detection. In one or more of the captured images, a defect point 720 can be detected with the benefit of the flash lamp and auto focus. The detection resolves the region into one or more defect points, hence completing the process of AOI-on-demand scan.

The defect regions that is to be scanned by the AOI-on-demand feature need not be linear regions as in FIG. 7(a) and 7(b). Other regions of arbitrary shapes are contemplated. FIG. 7(c) illustrates a rectangular zone which is covered by such a trajectory 722, which is serpentine. In such a case, an applicable algorithm determines a reasonable scan trajectory for the imaging channel to cover the area.

Figure 8:
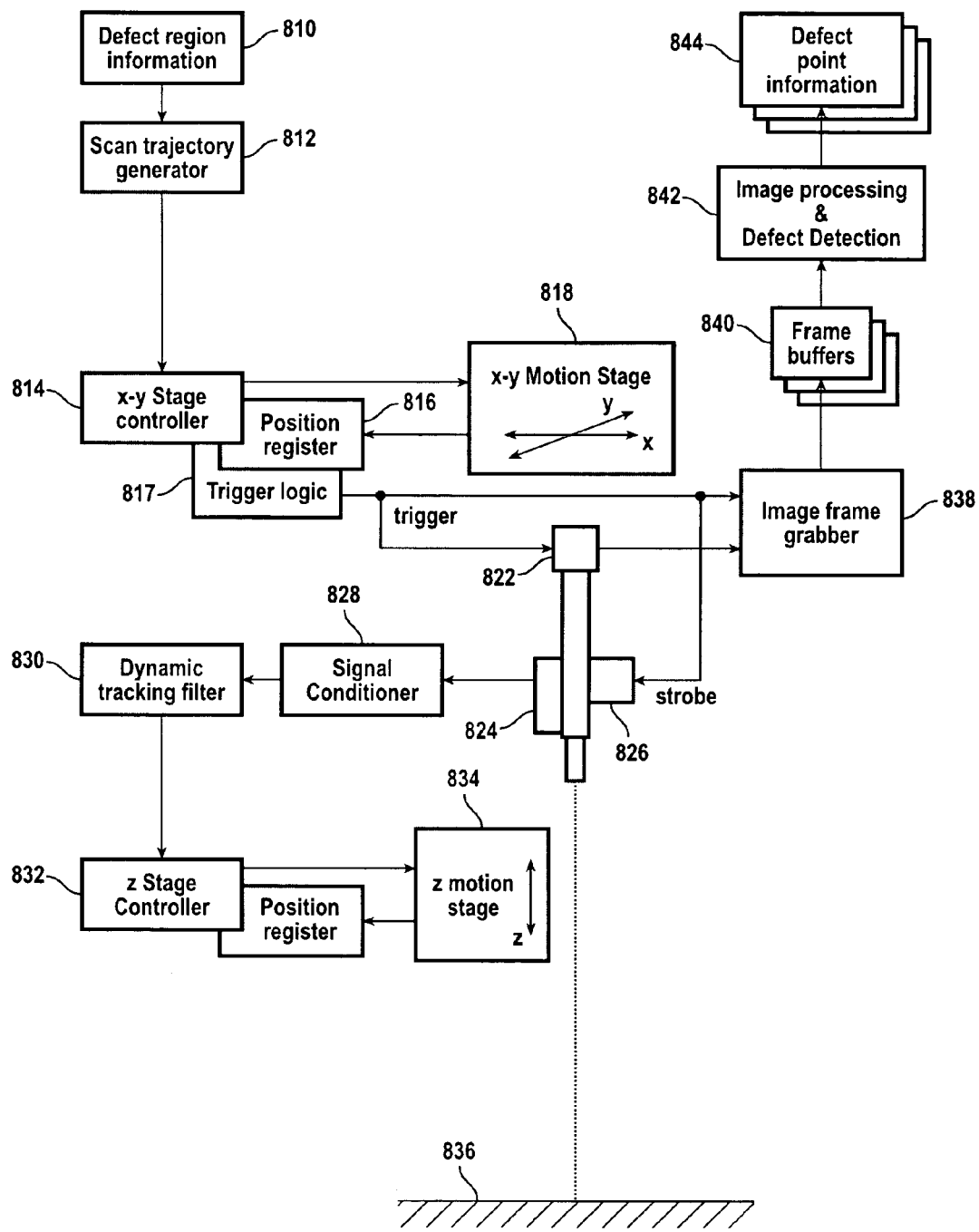
FIG. 8 is a diagram of the overall architecture of a specific embodiment of the invention.

The functional components of a specific embodiment of the invention are illustrated in FIG. 8. Initially, defect region information 810 is input to the system, specifying the region which could not be resolved into individual defect points. A scan trajectory generator 812 devises a suitable trajectory to cover the region with overlapping frames of fine resolution imaging, as dictated by the defect region information 810. The trajectory so generated drives an x-y stage controller 814 and moves the x-y stage 818 (or the platform bearing the subject element being inspected) to move the imaging channel relative to the subject element or material being inspected. A position register 816 and the associated trigger logic 817 tracks this instructed motion and generates the synchronized trigger signal 820 (714 in FIG. 7(a)). The signal is fed to the imaging sensor 822, an associated frame grabber 838 and flash light illuminator 826 to perform the synchronized image acquisition. During this strobe illuminated capture process, a hardware auto-focus sensor 824 feeds an in-focus quality signal (through an optional signal conditioner 828) to a dynamic tracking filter 830. The filter 830 generates in turn a sequence of set points for the z-axis controller 832 which drives the z-axis motion stage 834 to close the tracking auto-focus control loop. This setup maintains the best focus through the entire image capture process by adjusting the objective distance to the surface of the element being inspected 836. The captured frames are temporarily stored in dedicated frame buffers 840 and are processed by an applicable image processing and detection sub-system 842. This results in resolution of the original region to be resolved into records 844, 845, 846 flagged as individual defect point(s) and completes the entire process.

Precision inspection and repair instruments used in the application domains of electronic circuit wafer inspection or TFT LCD panel inspection are typically pre-equipped with an optical microscope and imaging hardware for defect review purposes. The camera of the present invention commonly has high magnification and resolution; however, it may also be equipped with a turret of various magnification objectives to change magnification on the fly.

To precisely locate and image sections of the subject being inspected or repaired, the instruments require that the subject be precisely aligned. This is typically achieved by use of locating and imaging alignment marks on the subject. The instrument may have a separate optical system for performing this function. Furthermore, since the alignment and review functions are not active concurrently with the proposed AOI-on-demand function, imaging channels are idle during the proposed AOI-on-demand period of the process.

Another embodiment uses the review camera as the imaging channel to collect the stream of images required for AOI-on-demand detection and localization. If the review system has only one magnification, the speed of the AOI-on-demand is determined by this magnification and may be too slow to be practical for a review camera of very high magnification. However, because it is a fully automatic process, it can be tolerated in some cases. The review camera may alternatively have a turret of objectives of different resolutions. In such cases, an objective with suitable magnification is selected by the AOI-on-demand sub-system to perform the scan.

Yet another hardware embodiment of the AOI-on-demand system uses the alignment camera as the imaging channel to collect the stream of images required for automatic optical defect detection and localization. The alignment camera is typically a monochrome camera with a magnification suitable, in selected cases, for the AOI-on-demand scan; hence it is a good candidate for this task.

Other embodiments with similar variations would be evident to those skilled in the art and are not explicitly listed in this document.

The present invention makes use of an available image processing algorithm to process the stream of images collected from the AOI-on-demand scan. The particular details of the particular algorithm to process the images and detect the defects are not of primary interest in the present invention. However, the magnification and resolution of the imaging channel is selected in accordance with the size of the smallest defects required to be detected. Because only a limited zone determined by the non-AOI methods is scanned by the sub-system, a higher magnification and imaging resolution can be used as compared with AOI systems capable of performing the scan of the entire surface of the article being inspected. Therefore, no sub-pixel alignment methods are necessary in case the defect detection method is based on conventional spatial comparison/pattern subtraction techniques. Other optical filtering techniques can be utilized as the defect detection means on the AOI-on-demand sub-system.

A calibration procedure and algorithm are used to integrate the AOI-on-demand sub-system to appropriate platforms. The particular details of such an algorithm are not subject of the present invention. However, the algorithm has all the provisions to relate the defect coordinates in reference to the collected images to the system wide global coordinates so that detected objects can be related with the non-AOI detected defects, can be mapped, can be reviewed by a microscope and can be displayed.

The invention has been explained with reference to specific embodiments. Other embodiments will be evident to those of ordinary skill in the art. It is therefore not intended that the invention be limited, except as indicated by the appended claims.

What is claimed is:

1. In a defect detection system for inspecting a planar electronic subject, the defect detection system being capable only of identifying a region that includes an anomaly on the subject being inspected and having an optical imaging channel of sufficient resolution to perform an automated optical inspection-on-demand, a method for inspecting the subject comprising:
   performing a first test to determine if a defect is present and whether the defect can be resolved into a point; if not,
   performing automated optical inspection-on-demand while performing a fine resolution optical review of the region by capturing area images of the region through the optical imaging channel optics using at least one pulse of illumination of short duration while scanning the region in order to resolve the region into at least one defect point.

2. The method according to claim 1 wherein the at least one pulse is a series used to illuminate a plurality of images in the region.

3. The method according to claim 1 further comprising continuously automatically focusing on the subject being inspected while scanning to maintain the subject in focus for each image.

4. The method according to claim 2 wherein a plurality of defect points are resolved from the plurality of images of the region.

5. The method according to claim 2 wherein the pulse of illumination has a duration of less than 8 microseconds for a continuous scanning speed of 30 mm per second.

6. In an optical inspection defect detection/repair system for inspecting a planar electronic subject, the defect detection system being capable only of identifying a region that includes an anomaly on the subject being inspected and having an optical imaging channel of sufficient resolution to perform an automated optical inspection-on-demand, an apparatus for inspecting the subject comprising:
 a tester to determine if a defect is present and whether the defect can be resolved into a point;
 an automated optical inspection-on-demand subsystem operative to dispatch inspection optics to a region of the defect, to capture and to store image data of the region of the defect to find at least one defect point, said subsystem including a fine resolution area imaging camera with a pulse illumination source disposed to scan the region and operative to capture area images illuminated with energy pulses of short duration while scanning the region for the defect.

7. In the system according to claim 6 wherein the energy pulse are a series used to illuminate a plurality of images in the region.

8. In the system according to claim 6, the subsystem further comprising hardware automatic focusing mechanism for continuously focusing on the subject being inspected while scanning.

9. In the system according to claim 7 further including a plurality of frame buffers for capturing a plurality of frames and a defect detector to resolve selected frames as a plurality of defect points from the plurality of images of the region.

10. In the system according to claim 7 wherein the pulse of illumination has a duration of less than 8 microseconds for a continuous scanning speed of 30 millimeters per second.

11. In a defect detection/repair system for inspecting and repairing a planar electronic subject, the defect detection system being capable only of identifying a region that includes an anomaly on the subject being inspected and having an optical imaging channel of sufficient resolution to perform an automated optical inspection-on-demand, an apparatus for inspecting the subject comprising:
 a tester to determine if a defect is present and whether the defect can be resolved into a point;
 an automated optical inspection-on-demand subsystem operative to dispatch inspection optics to a region of the defect, to capture and to store image data of the region of the defect to find a defect point, said subsystem including a fine resolution area imaging camera with a pulse illumination source disposed to scan the region and operative to capture area images illuminated with energy pulses of short duration while scanning the region for the defect and a hardware auto-focus sensor and controller for maintaining the subject in constant focus while scanning.

* * * * *